US010315018B2

(12) United States Patent
Eidenschink et al.

(10) Patent No.: US 10,315,018 B2
(45) Date of Patent: Jun. 11, 2019

(54) CATHETER SHAFT DESIGNS

(71) Applicant: BOSTON SCIENTIFIC SCIMED, INC., Maple Grove, MN (US)

(72) Inventors: Tracee E. J. Eidenschink, Wayzata, MN (US); Matthew C. Heidner, Maple Grove, MN (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 316 days.

(21) Appl. No.: 15/155,559

(22) Filed: May 16, 2016

(65) Prior Publication Data

US 2016/0296734 A1 Oct. 13, 2016

Related U.S. Application Data

(63) Continuation of application No. 11/535,811, filed on Sep. 27, 2006, now Pat. No. 9,339,632.

(51) Int. Cl.
*A61M 25/00* (2006.01)
*A61M 25/10* (2013.01)
(Continued)

(52) U.S. Cl.
CPC ......... *A61M 25/1025* (2013.01); *A61L 29/02* (2013.01); *A61L 29/14* (2013.01);
(Continued)

(58) Field of Classification Search
CPC .............. A61M 25/10; A61M 25/1025; A61M 25/1029; A61M 2025/0004; A61M 2029/1079
See application file for complete search history.

(56) References Cited

U.S. PATENT DOCUMENTS 4,547,193 A 10/1985 Rydell
4,580,551 A 4/1986 Siegmund et al.
(Continued)

FOREIGN PATENT DOCUMENTS

EP 0608853 A2 8/1994
EP 0778039 A1 6/1997
(Continued)

OTHER PUBLICATIONS

Webster's II New College Dictionary, p. 126, 1995.

*Primary Examiner* — Edelmira Bosques
(74) *Attorney, Agent, or Firm* — Seager, Tufte & Wickhem LLP.

(57) ABSTRACT

Disclosed is a balloon catheter that can comprise an elongate support member, an inflation tube, a guidewire tube and a balloon. The guidewire tube can define a guidewire port at its proximal end, and can extend from the port through an opening in a wall of the elongate support member and distally through a first lumen of the elongate support member, in some cases to the distal end of the catheter. The inflation tube can be disposed over a distal portion of the elongate support member, a portion of the guidewire tube, a portion of the inner assembly, or any combination thereof, forming a second lumen. The distal end of the balloon can be attached to the guidewire tube and the proximal end of the balloon can be attached to the inflation tube. The inside of the balloon can be in fluid communication with the first lumen and with the second lumen, allowing the balloon to be inflated and/or deflated. The elongate support member can also have cuts in it. For example, the elongate support member can have apertures formed in it, or apertures and spiral cuts.

20 Claims, 9 Drawing Sheets

(51) Int. Cl.
*A61M 29/02* (2006.01)
*A61L 29/02* (2006.01)
*A61L 29/14* (2006.01)
*A61L 29/18* (2006.01)
*A61M 25/01* (2006.01)

(52) U.S. Cl.
CPC ......... *A61L 29/18* (2013.01); *A61M 25/0028* (2013.01); *A61M 25/10* (2013.01); *A61M 29/02* (2013.01); *A61M 25/1029* (2013.01); *A61M 2025/0004* (2013.01); *A61M 2025/0183* (2013.01); *A61M 2025/1079* (2013.01)

(56) References Cited

U.S. PATENT DOCUMENTS

| | | |
|---|---|---|
| 4,753,238 A | 6/1988 | Gaiser |
| 4,795,439 A | 1/1989 | Guest |
| 4,998,923 A | 3/1991 | Samson et al. |
| 5,095,915 A | 3/1992 | Engelson |
| 5,228,441 A | 7/1993 | Lundquist |
| 5,238,004 A | 8/1993 | Sahatjian et al. |
| 5,315,996 A | 5/1994 | Lundquist |
| 5,322,064 A | 6/1994 | Lundquist |
| 5,328,472 A | 7/1994 | Steinke et al. |
| 5,329,923 A | 7/1994 | Lundquist |
| 5,334,145 A | 8/1994 | Lundquist et al. |
| 5,372,144 A | 12/1994 | Mortier et al. |
| 5,387,225 A | 2/1995 | Euteneuer et al. |
| 5,437,288 A | 8/1995 | Schwartz et al. |
| 5,477,856 A | 12/1995 | Lundquist |
| 5,490,837 A * | 2/1996 | Blaeser ............... A61M 25/104 604/103.11 |
| 5,507,751 A | 4/1996 | Goode et al. |
| 5,507,766 A | 4/1996 | Kugo et al. |
| 5,569,197 A | 10/1996 | Helmus et al. |
| 5,573,520 A | 11/1996 | Schwartz et al. |
| 5,741,429 A | 4/1998 | Donadio, III et al. |
| 5,772,669 A | 6/1998 | Vrba |
| 5,782,855 A | 7/1998 | Lau et al. |
| 5,788,707 A | 8/1998 | Del Toro et al. |
| 5,833,632 A | 11/1998 | Jacobsen et al. |
| 5,902,290 A | 5/1999 | Peacock, III et al. |
| 5,968,069 A | 10/1999 | Dusbabek et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,048,339 A | 4/2000 | Zirps et al. |
| 6,068,635 A | 5/2000 | Gianotti |
| 6,077,295 A | 6/2000 | Limon et al. |
| 6,096,045 A | 8/2000 | Del Toro et al. |
| 6,102,932 A | 8/2000 | Kurz |
| 6,123,712 A | 9/2000 | DiCaprio et al. |
| 6,168,617 B1 | 1/2001 | Blaeser et al. |
| 6,174,327 B1 | 1/2001 | Mertens et al. |
| 6,203,558 B1 | 3/2001 | Dusbabek et al. |
| 6,241,758 B1 | 6/2001 | Cox |
| 6,245,098 B1 | 6/2001 | Feeser et al. |
| 6,260,458 B1 | 7/2001 | Jacobsen et al. |
| 6,273,879 B1 * | 8/2001 | Keith ............... A61M 25/0662 600/435 |
| 6,287,291 B1 | 9/2001 | Bigus et al. |
| 6,287,315 B1 | 9/2001 | Wijeratne et al. |
| 6,302,893 B1 | 10/2001 | Limon et al. |
| 6,325,814 B1 | 12/2001 | Euteneuer et al. |
| 6,342,066 B1 | 1/2002 | Toro et al. |
| 6,371,962 B1 | 4/2002 | Ellis et al. |
| 6,398,802 B1 | 6/2002 | Yee |
| 6,428,489 B1 | 8/2002 | Jacobsen et al. |
| 6,428,566 B1 | 8/2002 | Holt |
| 6,431,039 B1 | 8/2002 | Jacobsen et al. |
| 6,436,090 B1 | 8/2002 | Sanchez et al. |
| 6,440,088 B1 | 8/2002 | Jacobsen et al. |
| 6,508,803 B1 | 1/2003 | Horikawa et al. |
| 6,514,280 B1 | 2/2003 | Gilson |
| 6,517,569 B2 | 2/2003 | Mikus et al. |
| 6,530,947 B1 | 3/2003 | Euteneuer et al. |
| 6,533,805 B1 | 3/2003 | Jervis |
| 6,562,064 B1 | 5/2003 | deBeer |
| 6,576,008 B2 | 6/2003 | Devonec et al. |
| 6,579,246 B2 | 6/2003 | Jacobsen et al. |
| 6,592,549 B2 | 7/2003 | Gerdts et al. |
| 6,592,568 B2 | 7/2003 | Campbell |
| 6,592,569 B2 | 7/2003 | Bigus et al. |
| 6,602,280 B2 | 8/2003 | Chobotov |
| 6,607,555 B2 | 8/2003 | Patterson et al. |
| 6,610,046 B1 | 8/2003 | Usami et al. |
| 6,623,491 B2 | 9/2003 | Thompson |
| 6,629,981 B2 | 10/2003 | Bui et al. |
| 6,652,508 B2 | 11/2003 | Griffin et al. |
| 6,660,031 B2 | 12/2003 | Tran et al. |
| 6,669,716 B1 | 12/2003 | Gilson et al. |
| 6,676,666 B2 | 1/2004 | Vrba et al. |
| 6,699,274 B2 | 3/2004 | Stinson |
| 6,702,802 B1 | 3/2004 | Hancock et al. |
| 6,712,827 B2 | 3/2004 | Ellis et al. |
| 6,723,071 B2 | 4/2004 | Gerdts et al. |
| 6,726,714 B2 | 4/2004 | DeCaprio et al. |
| 6,743,210 B2 | 6/2004 | Hart et al. |
| 6,746,423 B1 | 6/2004 | Wantink |
| 6,766,720 B1 | 7/2004 | Jacobsen et al. |
| 6,773,446 B1 | 8/2004 | Dwyer et al. |
| 6,802,849 B2 | 10/2004 | Blaeser et al. |
| 7,785,317 B2 | 8/2010 | Mitelberg |
| 2003/0069522 A1 | 4/2003 | Jacobsen et al. |
| 2003/0093059 A1 | 5/2003 | Griffin et al. |
| 2003/0093106 A1 | 5/2003 | Brady et al. |
| 2003/0125709 A1 | 7/2003 | Eidenschink |
| 2003/0176837 A1 | 9/2003 | Fitzmaurice et al. |
| 2004/0111044 A1 | 6/2004 | Davis et al. |
| 2004/0133158 A1 | 7/2004 | Keith et al. |
| 2004/0167437 A1 | 8/2004 | Sharrow et al. |
| 2004/0181174 A2 | 9/2004 | Davis et al. |
| 2005/0187602 A1 | 8/2005 | Eidenschink |
| 2005/0234499 A1 | 10/2005 | Olson et al. |
| 2006/0100687 A1* | 5/2006 | Fahey ............... A61F 2/95 623/1.11 |
| 2006/0129175 A1 | 6/2006 | Griffin et al. |

FOREIGN PATENT DOCUMENTS

| | | |
|---|---|---|
| EP | 0937481 A1 | 8/1999 |
| EP | 1144039 B1 | 12/2005 |
| WO | 9524236 A1 | 9/1995 |
| WO | 9744086 A2 | 11/1997 |
| WO | 03004086 A2 | 1/2003 |

* cited by examiner

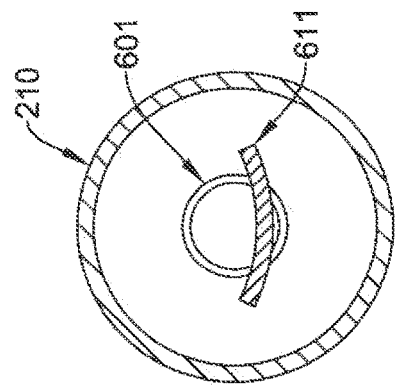
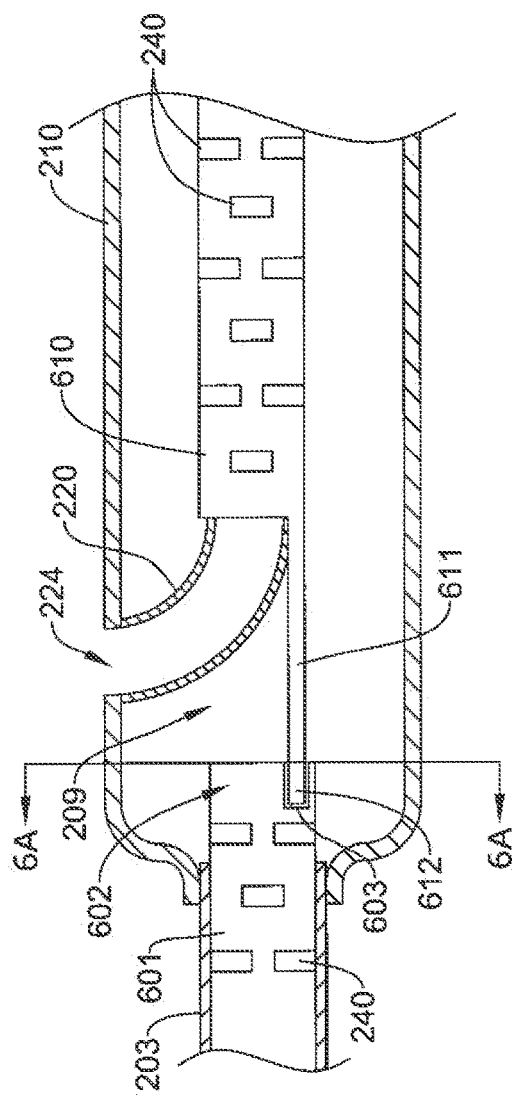

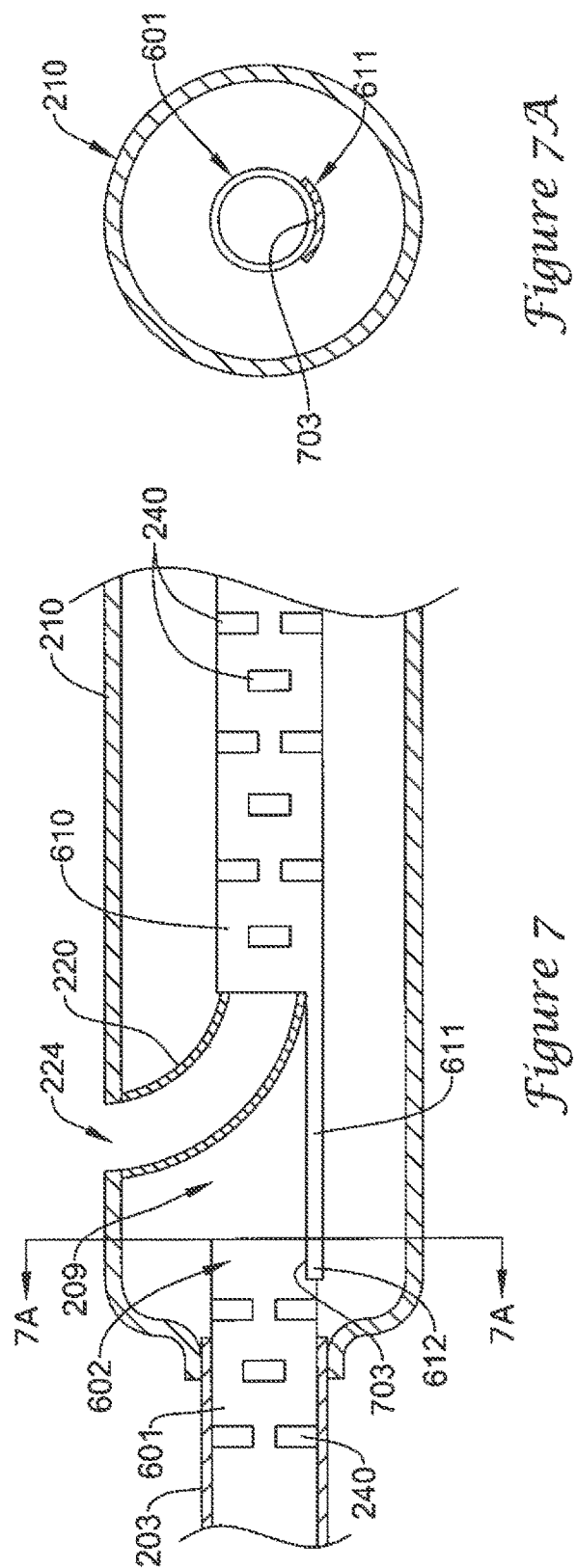

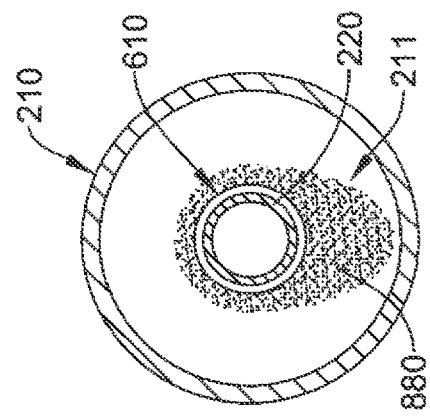
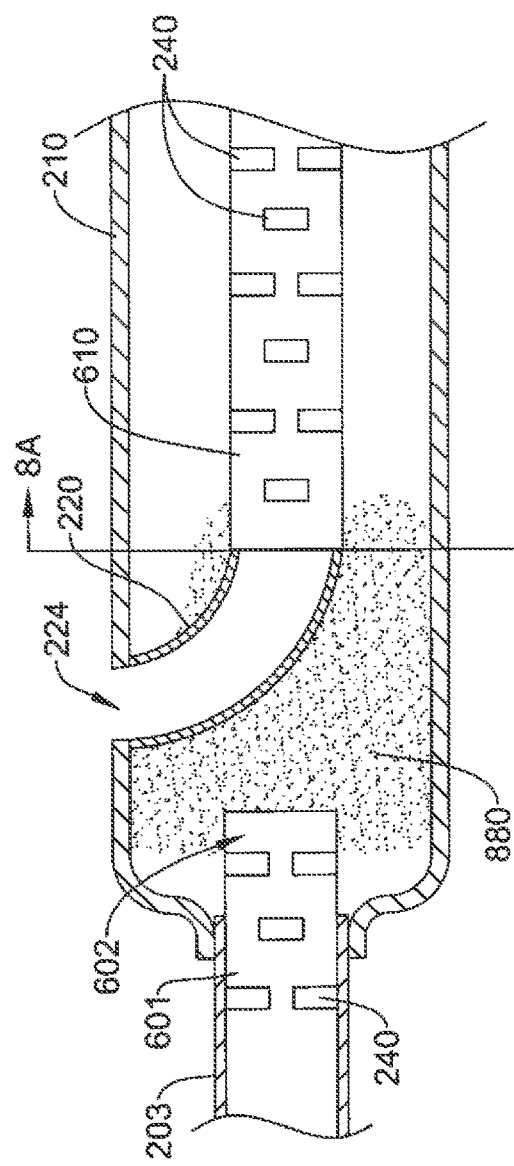

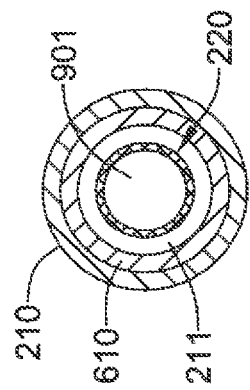
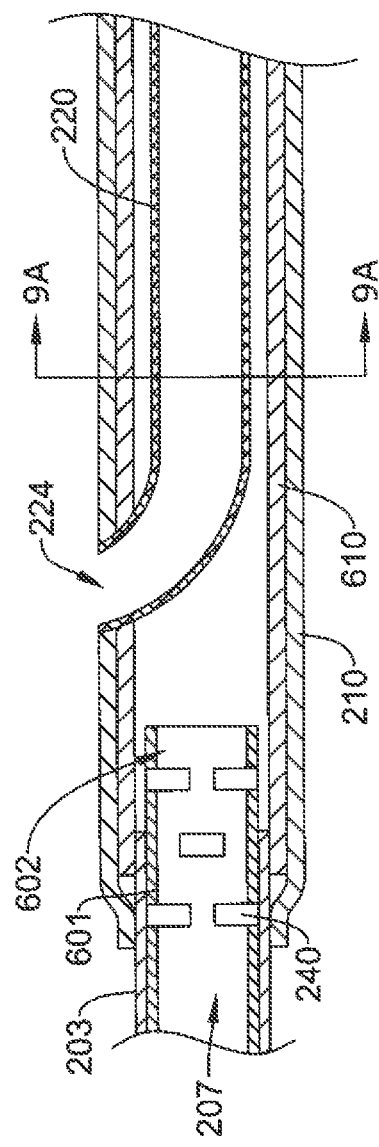

CATHETER SHAFT DESIGNS

RELATED APPLICATIONS

This application is a continuation of U.S. application Ser. No. 11/535,811 filed Sep. 27, 2006, now U.S. Pat. No. 9,339,632.

TECHNICAL FIELD

The technical field pertains generally to catheters. More specifically, it pertains to alternate catheter shaft designs.

BACKGROUND

A wide variety of medical devices such as catheters and guidewires have been developed. Medical devices such as catheters and guidewires can be used for performing intravascular procedures. These intravascular procedures have become commonly used in order to avoid more invasive surgical procedures. In some embodiments, a balloon is disposed at the end of a catheter or guidewire, and the balloon can be used for a variety of procedures. A number of different structures and assemblies for such balloon catheters and guidewires are known, each having certain advantages and disadvantages. However, there is an ongoing need to provide alternative structures, assemblies and methods.

SUMMARY OF SOME EMBODIMENTS

An example embodiment can be found in a balloon catheter that comprises an elongate support member, an inflation tube, a guidewire tube and a balloon. The elongate support member can extend from a proximal region of the catheter to a distal region of the catheter, and in some cases can define a first lumen along the length of the elongate support member. At least a portion of this first lumen can be a first inflation lumen. The guidewire tube can define a guidewire port at its proximal end, and can extend from the port through an opening in a wall of the elongate support member and distally through the first lumen of the elongate support member, in some cases to the distal end of the catheter. In some cases, the guidewire tube and the elongate support member can together form an inner assembly. Further, in some cases the elongate support member can be a hypotube, and in other cases the elongate support member can comprise multiple hypotubes that are attached to one another.

The inflation tube can be disposed over a distal region of the elongate support member, a portion of the guidewire tube, a portion of the inner assembly, or any combination thereof. In some cases the inflation tube can form an inflation lumen, for example an annular inflation lumen between the inflation tube and the elongate support member, between the inflation tube and the guidewire tube, between the inflation tube and the inner assembly, or any combination thereof. The distal end of the balloon can be attached to the guidewire tube and the proximal end of the balloon can be attached to the inflation tube. The inside of the balloon can be in fluid communication with the annular inflation lumen and with the first inflation lumen. These lumens can together form a fluid pathway, allowing the balloon to be inflated and/or deflated.

In another example embodiment, an inner assembly for a balloon catheter includes an elongate support member and a guidewire tube. The elongate support member has a proximal region and a distal region. The proximal region can have one or more cuts, and the distal region can have one or more cuts. The one or more cuts in the proximal region can differ from the one or more cuts in the distal region. For example, the cuts can differ based on one or more of the following characteristics: cut density, cut shape, cut angle, placement of the cuts relative to one another, and the type of cut. For example, at least a portion of the proximal region can have a plurality of rectangular cuts formed in the elongate support member, and at least a portion of the distal region can have a plurality of cuts of a greater density, which may allow for greater flexibility in the distal region. In another embodiment, at least a portion of the proximal region can have a plurality of rectangular cuts formed in the elongate support member, and at least a portion of the distal region can have one or more cuts of a different type, for example one or more spiral cuts.

The above summary of some embodiments is not intended to describe each disclosed embodiment or every implementation of the present invention. The Figures, and Detailed Description which follows, more particularly exemplify these and other embodiments.

BRIEF DESCRIPTION OF THE FIGURES

FIG. 6 is a cut away view of a portion of an alternative embodiment of a balloon catheter;

FIG. 6A is a cross-sectional view of the embodiment of FIG. 6;

FIG. 7 is a cut away view of a portion of an alternative embodiment of a balloon catheter;

FIG. 7A is a cross-sectional view of the embodiment of FIG. 7;

FIG. 8 is a cut away view of a portion of an alternative embodiment of a balloon catheter;

FIG. 8A is a cross-sectional view of the embodiment of FIG. 8;

FIG. 9 is a cut away view of a portion of an alternative embodiment of a balloon catheter; and FIG. 9A is a cross-sectional view of the embodiment of FIG. 9.

DETAILED DESCRIPTION OF SOME EMBODIMENTS

Figure 1:
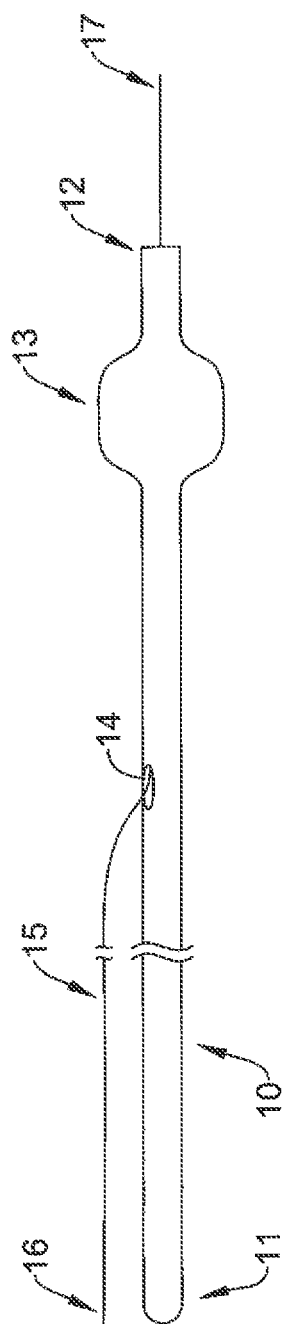
FIG. 1 is a perspective view of an embodiment of a catheter.

For the following defined terms, these definitions shall be applied, unless a different definition is given in the claims or elsewhere in this specification. The term "polymer" will be understood to include polymers, copolymers (e.g., polymers formed using two or more different monomers), oligomers and combinations thereof, as well as polymers, oligomers, or copolymers that can be formed in a miscible blend by, for example, coextrusion or reaction, including transesterification. Both block and random copolymers are included, unless indicated otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

Turning to FIG. 1, a perspective view of an example catheter is shown. The catheter has a shaft 10 with a proximal end 11 and a distal end 12, with a balloon 13 disposed proximate the distal end 12. The catheter can also define a guidewire lumen (not shown in FIG. 1) that extends along at least a portion of the catheter shaft 10. For example, the guidewire lumen can extend from a guidewire port 14 to the distal end of the catheter shaft 12. The guidewire port 14 can be disposed on the catheter shaft 10 between the catheter shaft proximal and distal ends (11, 12). Thus, in some cases the catheter can be a single operator exchange catheter. In one example, the guidewire port 14 can be disposed proximate the catheter shaft distal end 12, proximal of the balloon 13.

Figure 2:
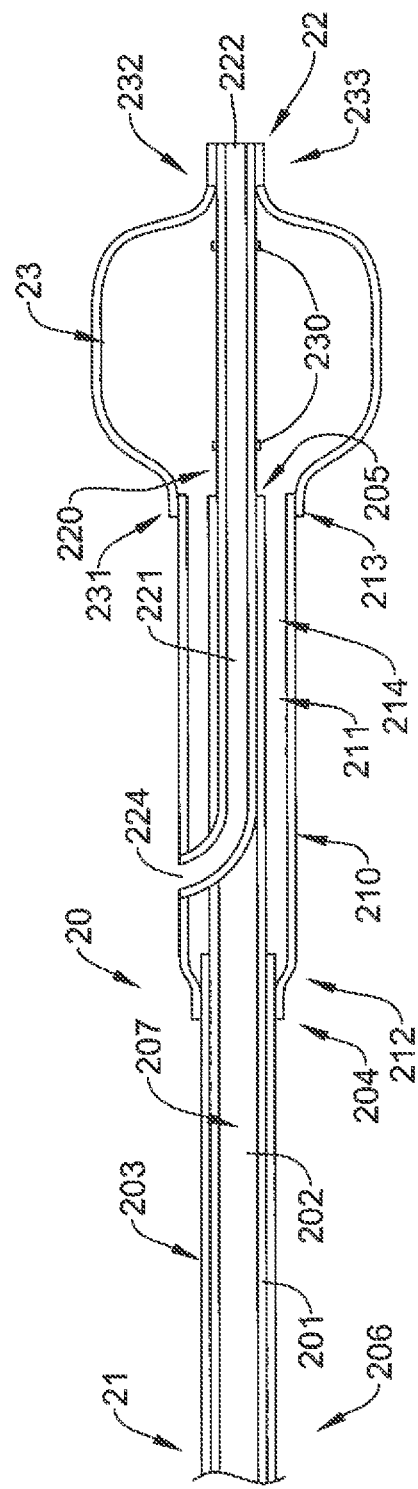
FIG. 2 is a cross-sectional view of a distal portion of another embodiment of a balloon catheter.

In FIG. 2, a cross-sectional view of an example embodiment of a catheter 20 with a proximal portion 21 and a distal region with a distal end 22 is shown. The catheter 20 includes an elongate support member 201 that defines a first lumen 202. At least a portion of this first lumen 202 can form a first inflation lumen 207. The elongate support member 201 can have a proximal portion 206 and a distal region including a distal end 205. As used herein, a proximal "region" or "portion" and a distal "region" or "portion" may generically refer to any two sections along any portion of the medical device that can be described as having a proximal/distal relationship to one another. In FIG. 2, the elongate support member 201 is shown as a hypotube 201 that extends from a proximal region of the catheter 20 to a distal region of the catheter.

The catheter 20 can also include a guidewire tube 220 that defines a guidewire lumen 221. The guidewire lumen 221 can extend from a proximal port 224 to a distal port 222. In some examples, the catheter 20 can further include an inflation tube 210 that defines a second lumen 211. At least a portion of the second lumen 211 can form a second inflation lumen 214. Further, the catheter 20 can be a balloon catheter and include a balloon 23 disposed proximate the catheter distal end 22.

The proximal port 224 can define an opening in the side of the inflation tube 210. The proximal end of the guidewire tube 220 can define the proximal port 224, and the guidewire tube 220 can extend from the proximal port 224 through an opening 209 (shown in detail in FIG. 3) in the wall of the hypotube 201 and into the hypotube lumen 202. The guidewire tube 220 can also extend distally through the hypotube lumen 202 and through at least a portion of the balloon 23. Optionally, the guidewire tube 220 can extend through and distal of the balloon 23. In some cases, the hypotube 201 and the guidewire tube 220 can together form an inner assembly.

The inner assembly can be formed by disposing at least a portion of the guidewire tube 220 within a portion of the hypotube lumen 202. For example, the opening 209 can be formed in a side wall of the hypotube 201, for example by cutting away a portion of the side wall, and a distal portion of the guidewire tube 220 can be passed through the opening 209. Additional length of the guidewire tube 220 can be passed through the opening 209 and into the lumen 202 so that the guidewire tube 220 can extend distally through the lumen 202 of the hypotube 201. Methods of forming other examples of inner assemblies are described below.

The inflation tube 210 can be disposed over a portion of the length of the hypotube 201, over a portion of the length of the guidewire tube 220, over a portion of the length of the inner assembly, or any combination thereof. For example, the inflation tube 210 can be disposed over at least a portion of the hypotube 201 and at least a portion of the guidewire tube 220, forming a second lumen 211. The second lumen 211 can be defined by the inner surface of the inflation tube 210 and at least a portion of the outer surface of the hypotube 201 and/or at least a portion of the outer surface of the guidewire tube 220. This lumen 211 can be an inflation lumen 214, and in some cases can be annularly shaped. The inflation tube proximal end 212 can be attached to the hypotube 201 at an intermediate region that can be located between proximal and distal regions of the hypotube 201. For example, this attachment can occur at an intermediate connection zone 204. This bond between the hypotube intermediate connection zone 204 and the inflation tube 210 can be formed in any known manner, including by using adhesive, welding (for example, laser welding), mechanical coupling, mechanical bonding such as crimping or any combination thereof.

In addition, in the example embodiment of FIG. 2, the balloon 23 can be attached to the catheter proximate the catheter distal end 22. The balloon can have a distal waist 232 and a proximal waist 231. In one example, the distal waist 232 can be attached to the inner assembly. For example, the distal waist 232 can be attached along an attachment zone 233 to a distal portion of the hypotube 201 or, as shown in FIG. 2, a distal portion of the guidewire tube 220, or both. Some possible designs for the distal end portion of the catheter will be further described below. The proximal waist 231 of the balloon 23 can be attached to the inflation tube distal end 213. The interior of the balloon 23 can be in fluid communication with the first and second inflation lumens (202, 211), creating a fluid pathway that allows the balloon 23 to be inflated and deflated. The attachment of the balloon to other structures of the catheter 20 can be by any known manner, including adhesive, welding (for example, laser welding), mechanical coupling, mechanical bonding such as crimping or any combination thereof.

Figure 3:
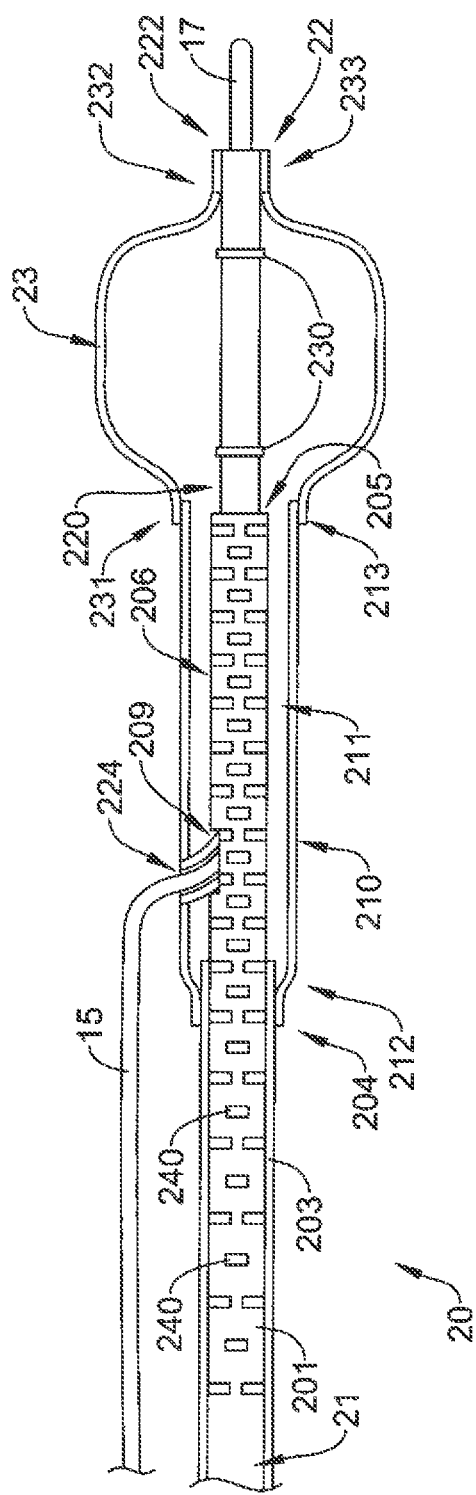
FIG. 3 is a partial cut-away view of a distal portion of the catheter of FIG. 2.

Referring to FIG. 3, the catheter of FIG. 2 is shown in partial cut-away view. In some cases, it is desirable to provide certain properties (i.e., flexibility, torque transmission, etc.) at certain points along the length of the catheter. In some embodiments, it is desirable to vary properties (i.e., flexibility, torque transmission, etc.) of the catheter along the length of the catheter. In some embodiments, the design and placement of the hypotube 201 can be controlled in order to provide a catheter 20 with the desired properties.

In the example of FIG. 3, the elongate support member 201 (shown as a hypotube 201) extends distally from a proximal portion 21 of the catheter 20. In some alternative embodiments, the elongate support member 201 can extend distally from the proximal end (not shown) of the catheter 20. The elongate support member distal end 205 can extend distally to a point proximate the inflation tube distal end 213, or to a point proximate the balloon proximal waist 231, or both. In other embodiments, the elongate support member distal end 205 can extend farther distally, for example, to a point inside the balloon 23 and/or to the balloon distal waist 232. The elongate support member distal end 205 can also extend to a point distal of the balloon distal waist 232 and/or to the distal end 22 of the catheter 20. Further, the location of the elongate support member distal end 205 can also be described in other ways; for example, the elongate support member distal end 205 can be located distal of the guidewire port 224 or between the guidewire port 224 and the proximal balloon waist 231. Any of these positions of the elongate support member distal end 205 can be combined with any of the positions for the elongate support member proximal end, as described above, depending on the desired characteristics of the catheter shaft. Further, it is contemplated that the elongate support member can comprise multiple tubular members that are attached to form the elongate support member.

One of ordinary skill in the art would recognize that any of these positions for the elongate support member proximal end or distal end 205 could be chosen depending on the desired properties of the catheter shaft. For example, maintaining the hypotube distal end 205 proximal of the balloon 23 may allow the distal portion of the catheter to be more flexible. In such cases, the guidewire tube 220 can extend through the balloon 23, and in some cases on to the catheter distal tip 22. If the guidewire tube 220 comprises flexible material and/or construction, it can provide for a catheter with a flexible distal portion. If the hypotube distal end 205 is positioned at or near the distal end 22 of the catheter 20, then, with the support of the hypotube 201, the distal tip of the catheter 20 may be stiffer, allowing the catheter 20 to be used for other procedures, for example crossing lesions. Further, in some embodiments it is contemplated to have the distal end of the hypotube 205 end distal of the distal end of the guidewire tube 220, and thus the distal port can be formed by the hypotube distal end 205.

Along with the placement of the elongate support member 201, the design of the elongate support member 201 can also be used in order to adjust the stiffness of all or portions of the catheter 20 and/or vary the stiffness along the length of the catheter 20. In FIG. 3, for example, the hypotube 201 may include a thin wall tubular structure including one or more apertures or cuts 240, for example grooves, slits, slots, holes, openings, or the like, formed in a portion of, or along the entire length of, the hypotube 201. The apertures or cuts 240 can be formed in essentially any known way. For example, apertures or cuts 240 can be formed by methods such as micro-machining, saw-cutting, laser cutting, grinding, milling, casting, molding, chemically etching or treating, drilling, or other known methods, and the like.

In some embodiments, the apertures or cuts 240 can completely penetrate the body wall of the hypotube 201. In other cases, only some of the apertures or cuts 240 completely penetrate the body wall. In such cases, some or all of the apertures or cuts 240 may only partially extend into the body wall of the hypotube 201, either on the interior or exterior surface thereof. The shape and size of the apertures or cuts 240 can vary to achieve the desired characteristics. For example, the shape of apertures or cuts 240 can vary to include essentially any appropriate shape, such as squared, round, rectangular, pill-shaped, oval, polygonal, elongate, irregular, spiral (which may or may not vary in pitch), or other suitable means or the like, and may include rounded or squared edges, and can be variable in length and width, total open area, and the like.

In some embodiments, some adjacent apertures or cuts 240 can be formed such that they include portions that overlap with each other about the circumference of the hypotube 201. In other embodiments, some adjacent apertures or cuts 240 can be disposed such that they do not necessarily overlap with each other, but are disposed in a pattern that provides the desired degree and/or direction of lateral flexibility. For example, the apertures or cuts 240 can be arranged in a symmetrical pattern, such as being disposed essentially equally on opposite sides about the circumference of the hypotube 201, or equally spaced along the length of the hypotube 201.

As can be appreciated, the spacing, arrangement, and/or orientation of the apertures or cuts 240 can be varied to achieve the desired characteristics. For example, the number, proximity (to one another), density, size, shape and/or depth of the apertures or cuts 240 along the length of the hypotube 201 may vary in either a stepwise fashion or consistently, depending upon the desired characteristics. For example, the number or proximity of apertures or cuts 240 to one another near one end of the hypotube 201 may be high, while the number or proximity of apertures or cuts 240 to one another at another longitudinal location along the hypotube 201 may be relatively low. In the some embodiments, portions closer to the hypotube distal end 205 may include a greater density of apertures or cuts 240, while hypotube proximal regions may include a lesser density of apertures or cuts 240, or may even be devoid of any apertures or cuts 240. As such, the portions of the hypotube closer to the distal end 205 can have a greater degree of lateral flexibility relative to hypotube proximal regions.

In the embodiment shown in FIG. 3, the apertures or cuts 240 are disposed in a generally uniform pattern along the length of a distal portion of the hypotube 201, with a greater aperture or cut density at a distal portion of the hypotube 201 compared to a proximal portion. In this embodiment, the apertures or cuts 240 can have a length and a width, and the length of the apertures or cuts can extend generally perpendicular to the longitudinal axis of the hypotube 201. In other words, the apertures or cuts 240 can have a major axis extending along their length that extends radially about the longitudinal axis of the hypotube 201, and the major axis is generally perpendicular to the longitudinal axis of the hypotube 201.

Additionally, in the embodiment shown, the apertures or cuts 240 are formed in groups of two, wherein each of the two apertures or cuts 240 in the group is disposed at a similar longitudinal point along the length of the hypotube 201, but on opposite sides of the tubular member about the circumference thereof. Adjacent pairs of apertures or cuts 240 can be rotated by 90 degrees, or by less than 90 degrees, for example 80, 85 or 89 degrees. It should be understood, however, that in other embodiments the arrangement of the apertures or cuts can be varied to achieve the desired characteristics along the length of the hypotube 201. For example, instead of pairs, only a single aperture or cut, or more than two apertures or cuts, may be located at certain points along the length of the device. Additionally, the major axis of the apertures or cuts may be disposed at different angles, not necessarily perpendicular to the longitudinal axis of the hypotube 201.

Collectively, this Description illustrates that changes in the arrangement, number, and configuration of apertures or cuts 240 may vary without departing from the scope of the invention. Some additional examples of arrangements of apertures or cuts formed in a tubular body are disclosed in U.S. Pat. No. 6,428,489, and in U.S. Pat. No. 6,579,246, both of which are hereby incorporated by reference in their entirety. Also, some additional examples of arrangements of apertures or cuts formed in a tubular body for use in a medical device are disclosed in a U.S. patent application Ser. No. 10/375,493 filed Feb. 28, 2003 (Pub. No. US 2004/0167437), which is hereby incorporated by reference in its entirety.

The flexibility characteristics of the tubular member 21 could be achieved using any combination of the above apertures or cuts 240, or by using other methods, such as by the addition of material, by using one or more reinforcement members along certain portions of the hypotube 201, by providing a hypotube with a tapered-thickness wall, or by any combination of these methods.

Referring again to FIG. 3, the hypotube 201 has no apertures or cuts formed in it in a proximal portion 21 of the hypotube 201. Apertures or cuts 240 are formed in the hypotube 201 beginning at a point proximal of the intermediate connection zone of the hypotube 201. From this point, the apertures or cuts 240 are formed in increasing density in the distal direction. The portion of the hypotube that is proximal of the intermediate connection zone can be covered with an additional tubular member and/or a coating material 203. This additional tubular member and/or coating material 203 can seal any apertures or cuts 240 that are formed in the hypotube proximal of the intermediate connection zone 204, forming a fluid tight lumen 202 at least up to the point of the intermediate connection zone 204. The additional tubular member and/or coating material 203 can extend distally to or through the intermediate connection zone 204, or it can extend past the intermediate connection zone 204. As shown in the example embodiment of FIG. 3, the proximal end 212 of the inflation tube 210 can be attached to the additional tubular member and/or coating material 203. In other examples, the inflation tube 210 can be connected directly to the surface of the hypotube 201. It is also contemplated that the apertures or cuts 240 that are proximal of the intermediate connection zone 204 can be formed through only a portion of the thickness of the hypotube wall. Thus, in some cases the flexibility of the hypotube 201 can be altered, in some examples while maintaining a fluid tight lumen 202 up to the intermediate connection zone 204. Additionally, in other example embodiments, the hypotube can have no apertures or cuts 240 formed in it proximal of the intermediate connection zone 204. In such cases, the additional tubular member and/or coating material 203 may or may be present.

The outer surface of the remainder of the hypotube 201 that is distal of the additional tubular member and/or coating material 203 can be uncovered. For example, the outer surface of the portion of the hypotube 201 that is distal of the intermediate connection zone 204 can be uncovered. In these portions that are uncovered, fluids from the first inflation lumen 207 can be allowed to escape through the apertures cuts 240 and into the second inflation lumen 214. In this way, fluid can be communicated down the first inflation lumen 207 of the hypotube 201, through the open apertures or cuts 240, into the second inflation lumen 214 and into the open space of the balloon 23.

An additional method of imparting flexibility in the hypotube 201 is to make a helical cut in the hypotube 201. The helical cut could extend through the entire thickness of the wall of the tubular member 21, or only partially through the wall. The helical cut can also have a pitch, and the pitch can be constant or can vary along the length of the tubular member. For example, the pitch of the helical cut can change, making adjacent cuts of the helical cut closer together at a distal portion of the hypotube 201 compared to a proximal portion of the hypotube 201, or vice versa.

In some cases, the hypotube can have a proximal portion and a distal portion where the proximal portion can have one or more cuts and the distal portion can have one or more cuts. The one or more cuts in the proximal portion can differ from the one or more cuts in the distal portion. For example, the cuts can differ based on one or more of the following characteristics: cut density, cut shape, cut angle, placement of the cuts relative to one another, and the type of cut. In some examples, at least a portion of the proximal portion can have a plurality of apertures or cuts of a first density formed in the hypotube, and at least a portion of the distal portion can have a plurality of cuts of a second, greater density, which may allow for greater flexibility in the distal portion. In another embodiment, at least a portion of the proximal portion can have a plurality of apertures of cuts formed in the hypotube, and at least a portion of the distal portion can have one or more cuts of a different type, for example one or more spiral cuts.

In some cases, an opening 209 in the hypotube 201 for the guidewire tube 220 to pass through can mark the division between a proximal portion with one or more cuts formed in it and a distal portion with one or more cuts formed in it where the cuts of the proximal portion and distal portion differ from one another, for example as discussed herein. In other cases, the opening 209 in the hypotube 201 for the guidewire tube 220 can be located in a proximal portion with one or cuts formed in it or in a distal portion with one or more cuts formed in it, where the cuts of the proximal portion and the distal portion differ from one another, for example as discussed herein.

In addition to the placement and the design of the hypotube 201, the materials of construction for each of the elements of the catheter 20 can also affect the properties (e.g., the level of flexibility, torque transmission, etc.) of the catheter 20. The materials that can be used for the various components of catheter 20 may include those commonly associated with medical devices. These materials will be further described below.

Figure 4:
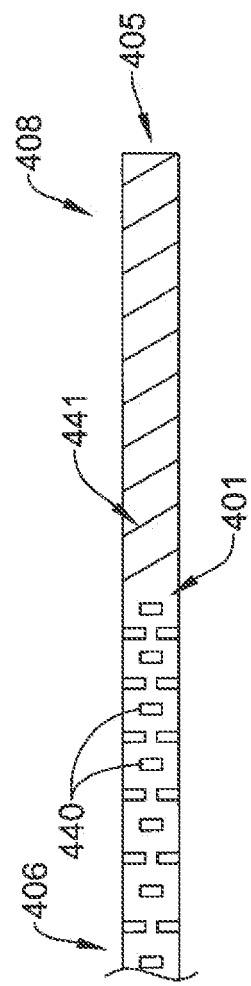
FIG. 4 is a perspective view of an embodiment of a hypotube.

Turning now to FIG. 4, an elongate support member is shown in perspective view, and comprises a hypotube 401. The hypotube 401 can have a proximal portion 406, a distal portion 408, and a distal end 405. The proximal portion 406 can have one or more cuts 440 formed therein and the distal portion 408 can have one or more cuts 441 formed therein. In some embodiments, the cuts of the proximal portion 406 can differ from the cuts of the distal portion 408. For example, the cuts can differ based on one or more of the following characteristics: cut density, cut shape, cut angle, placement of the cuts relative to one another, and the type of cut. In the example embodiment of FIG. 4, at least a portion of the proximal portion 406 can have a plurality of apertures or cuts 440 formed in the hypotube 401, and at least a portion of the distal portion 408 can have one or more cuts 441 of a different type, for example one or more spiral cuts 441. The plurality of apertures or cuts 440 can be formed in any of the patterns mentioned above, including a pattern of increasing density of apertures or cuts 440 in the distal direction. The one or more spiral cuts 441 can have a proximal end near where the plurality of cuts of the proximal portion 406 ends, and the one or more spiral cuts 441 can extend a portion, or the entire, way to the hypotube distal end 405. The one or more spiral cuts 441 can be formed in any of the patterns mentioned herein, including a pitch that can change along the length of the spiral cut, forming closer spiral windings in distal portions compared to proximal portions of the hypotube 201. It is also contemplated that a portion of the hypotube 401 can have more than one spiral cuts, for example 2, 3, or 4 spiral cuts, along its length. The embodiment shown in FIG. 4 and the additional embodiments described above can be incorporated as a hypotube, or as a portion of a hypotube, into any of the embodiments described herein.

Figure 5:
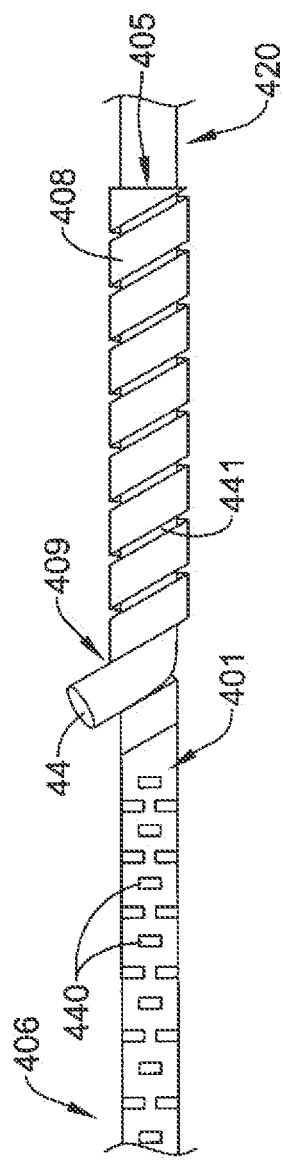
FIG. 5 is a perspective view of an inner assembly.

Turning now to FIG. 5, the hypotube 401 of FIG. 4 is shown with a guidewire tube 420 disposed within a distal portion 408 of the hypotube 401. The hypotube distal portion 408 with a spiral cut 441 can be wrapped around the guidewire tube 420. For example, the proximal end of the guidewire tube 420 can define a port 44. The guidewire tube 420 can extend from this port 44 through an opening 409 in the hypotube 401 (which can be defined by a space created by separating a spiral cut 441), and distally down a lumen formed by the spiral cut hypotube distal portion 408.

In some cases, the hypotube distal portion 408 can have an initial inner diameter. Due to the spiral cut in the hypotube distal portion 408, the distal portion 408 can accommodate a guidewire tube 420 that has a larger outer diameter than the initial inner diameter of the hypotube 401. For example, as shown in FIG. 5, the spiral cut portion of the hypotube 401 can expand in order to accommodate the guidewire tube 420. In some cases, this can allow the hypotube proximal portion 406 to have a smaller profile, while allowing the hypotube distal portion 408 to accommodate a guidewire tube 420 with an outer diameter larger than the inner diameter of the hypotube. The guidewire tube 420 and the hypotube 401 can together form an inner assembly.

In a method of making an inner assembly, a portion of a hypotube with a spiral cut in the distal end (e.g., the hypotube 401 shown in FIGS. 4 and 5) can be disposed over at least a portion of a guidewire tube. In order to dispose a portion of the hypotube over a guidewire tube, the spiral cut at the distal end of the hypotube can be started over the guidewire tube. The hypotube can be rotated with respect to the guidewire tube, advancing the hypotube spiral cut over the guidewire tube to the desired point, for example at or near the proximal end of the spiral cut. This method can result in an inner assembly for a catheter that has a guidewire tube extending through an opening in the side of a hypotube and extending distally down the hypotube.

Further, any of the inner assemblies described in this application can be incorporated into a catheter, for example any of the catheter designs mentioned herein. An inflation tube can be disposed over the inner assembly, creating a lumen therebetween. In some cases, a proximal portion of the hypotube can have an additional tubular member and/or a coating disposed over it, for example from a proximal end to an intermediate connection zone. A balloon can be attached to the distal end of the catheter shaft. For example, a proximal portion of the balloon can be attached to the inflation tube and the distal portion of the balloon can be attached to the inner assembly and/or to a distal tip structure.

In another embodiment, a balloon catheter, for example any of the balloon catheters described herein, includes a guidewire. The guidewire can, as shown in FIG. 1, be shaped and configured, and be of sufficient length, to pass along the side of the catheter 10, enter into the guidewire port 14, extend distally through a guidewire lumen (not shown in FIG. 1), and pass out the distal end of the catheter 10. Such an embodiment can be used, for example, in forming a single operator exchange type catheter.

Referring again to FIG. 1, any of the embodiments of catheters described herein can have any number of possible distal tip 12 configurations. For example, a distal tip 12 can be designed to be atraumatic. In such an embodiment, a hypotube or another portion of an elongate support member can end proximal of the distal tip in order to affect the stiffness of the distal tip 12 as little as possible. The distal tip 12 can have a guidewire tube extending through, and distal of, the balloon 13. The guidewire tube can be flexible, thus providing an atraumatic distal tip 12. In other embodiments, a distal tip member can be attached to the distal end of a guidewire tube, and/or to the distal portion of the balloon 13. In such a case, the distal extremity of the guidewire tube can be proximate the distal waist of the balloon 13, inside the balloon 13, proximate the proximal waist of the balloon 13, or even proximal of the balloon 13. This distal tip member can provide for an atraumatic distal tip 12. The guidewire tube or any separate distal tip member can be atraumatic by being made of material that is sufficiently flexible, by providing a tapered shape or other atraumatic shape, or by providing both a flexible and a shaped distal tip. Any of the distal tip designs can be incorporated into any of the device designs described herein. Further, a portion of the elongate support member, for example a distal end of a hypotube of the elongate support member, can extend to a point inside the balloon, to proximate the distal end of the entire device, or to the distal end of the entire device. The position that is chosen for the distal end of the elongate support member can vary depending on the stiffness that is desired at the distal tip. For example, if it is desirable to provide a distal tip that can push through occlusions in the vasculature, then the elongate support member can extend to a point proximate, or all the way to, the distal end of the device.

For example, the elongate support member 201, inflation tube 210, guidewire tube 220, or any combination thereof, can be made from a polymer, a metal, a metal alloy, a metal-polymer composite, or any other suitable material. Some examples of suitable metals and metal alloys include stainless steel, such as 304V, 304L, and 316LV stainless steel; mild steel; nickel-titanium alloy such as linear-elastic or super-elastic Nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 625, or the like; other Co—Cr alloys; platinum enriched stainless steel; or other suitable material.

Within the family of commercially available nickel-titanium or Nitinol alloys is a category designated "linear elastic" which, although it may be similar in composition to conventional shape memory and superelastic varieties, exhibits distinct and useful mechanical properties. By the applications of cold work, directional stress, and heat treatment, the material is fabricated in such a way that it does not display a substantial "superelastic plateau" or "flag region" in its stress/strain curve. Instead, as recoverable strain increases, the stress continues to increase in a generally linear relationship (as compared to that of super-elastic material, which has a super-elastic plateau) until plastic deformation begins. In some embodiments, the linear elastic nickel-titanium alloy is an alloy that does not show any substantial martensite/austenite phase changes that are detectable by DSC and DMTA analysis over a large temperature range.

For example, in some embodiments, there are no substantial martensite/austenite phase changes detectable by DSC and DMTA analysis in the range of about .about.60.degree. C. to about 120.degree. C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy. Accordingly, components of catheter 20 such as inflation tube 210 and/or guidewire tube 220 and/or hypotube 201 may include linear elastic nickel-titanium alloy.

In some embodiments, the linear elastic nickel-titanium alloy is in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are hereby incorporated by reference in their entirety. In some other embodiments, a superelastic alloy, for example a superelastic Nitinol can be used to achieve desired properties.

Some examples of suitable polymers can include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PFA), polyether-ester, some adhesive resin such as modified polyolefin resin, polymer/metal composites, etc., or mixtures, blends or combinations thereof, and may also include or be made up of a lubricous polymer. Some other potentially suitable polymer materials may include those listed herein with reference to other components of the catheter 10. One example of a suitable polyether block ester is available under the trade name ARNITEL, and one suitable example of a polyether block amide (PEBA) is available under the trade name PEBAX®, from Atomchem Polymers, Birdsboro, Pa. In some embodiments, adhesive resins may be used, for example, as tie layers and/or as the material of the structures. One example of a suitable adhesive resin is a modified polyolefin resin available under the trade name ADMER®, from Mitsui Chemicals America, Inc. Additionally, polymer material can, in some instances, be blended with a liquid crystal polymer (LCP). For example, in some embodiments, the mixture can contain up to about 5% LCP. This has been found in some embodiments to enhance torqueability. Components of the catheter 20, such as the elongate support member 201, the additional tubular member and/or coating 203, the inflation tube 210, the guidewire tube 220, or any combination thereof, can incorporate any of the above polymers.

In some embodiments, the elongate support member 201 can incorporate any one or more of the metal or metal alloy materials described herein and the inflation tube 210, the guidewire tube 220 and the additional tubular member and/or coating 203 can incorporate any one or more of the polymer or other non-metal material that are described herein. For example, the elongate support member 201 can comprise a Nitinol tube that has linear elastic, superelastic or shape memory characteristics at the temperature of use, for example at 35.degree. C., 37.degree. C. or 40.degree. C. In addition, some embodiments can have different properties in different portions of a Nitinol tube. For example, a proximal portion of the elongate support member 201 can have superelastic properties and a distal portion of the hypotube 201 can have linear elastic properties at the temperature of use, for example at 35.degree. C., 37.degree. C. or 40.degree. C. The elongate support member 201 can also comprise stainless steel.

In some cases, a hypotube can extend from a proximal region to a distal region of the catheter. For example, a hypotube can extend along the shaft in any manner discussed above with respect to FIGS. 2 and 3. The hypotube in these examples can be described as monolithic structures, or structures that comprise one continuous hypotube. In some other examples, an elongate support member can comprise more than one member, for example more than one hypotube joined together to form the elongate support member. In any case, a proximal and/or distal tubular member can be joined to the hypotube. In some embodiments, the elongate support member 201 can have a stainless steel proximal region (e.g., a stainless steel hypotube) and a Nitinol tube (e.g., a Nitinol hypotube) as a distal region, comprising, for example, any of the Nitinol alloys mentioned herein. The distal portion could be, for example, the portion of the elongate support member 201 that is shown in FIGS. 2 and 3. In this manner, the elongate support member 201 can be formed from one tube or from multiple tubes, such as 2, 3, or 4 tubes that have been attached to one another in any known fashion, for example by welding, soldering, mechanical engagement, friction fit between tubes, by use of a connector element, or by any combination thereof.

In the examples where the elongate support member comprises two or more tubular members (e.g., two or more hypotubes), the elongate support member can comprise at least a distal tube and a proximal tube. As used herein, the terms distal tube and proximal tube refer to tubes that are disposed along a distal or proximal region, respectively, of the shaft. The proximal tube can extend from a proximal region of the catheter and distally to a point that is at, proximate, or distal an intermediate portion, for example an intermediate connection zone, of the elongate support member. The distal tube can extend from the distal end of the proximal tube, or a longitudinal space could be formed between them, or another structure could be placed therebetween.

Some example embodiments of some multi-tubular structures will be described in further detail in FIGS. 6-8A, wherein common reference numerals can refer to similar structure to the embodiments discussed above. In these figures, like reference numerals refer to like structure. In FIG. 6, the elongate support member comprises a proximal hypotube 601 and a distal hypotube 610. It can be desirable in some cases to provide for longitudinal engagement between the proximal 601 and distal 610 hypotubes, for example so that axial forces can be effectively transmitting down the shaft of the catheter. Such longitudinal engagement can be by a direct connection of the hypotubes, by placing the hypotubes in contact with one another and/or attaching them to one another, or by placing a separate connecting member in between the two hypotubes.

FIG. 6 shows an elongate support member with proximal and distal hypotubes (601, 610). In this example, the distal hypotube 610 has a proximal end 612 that can comprise a stinger 611. The stinger 611 can extend proximally to come into contact with the proximal hypotube. The stinger 611 can be formed from the distal hypotube by cutting a portion of the distal hypotube 610 away, leaving a notch or opening 209. This notch or opening 209 can be similar to the notch or opening 209 described with respect to other embodiments herein. Thus, in cases where the stinger 611 is formed by cutting away a portion of the distal hypotube 610, the tubular portion of the distal hypotube and the stinger 611 can be referred to as a monolithic or one-piece structure. It is also contemplated that the stinger 611 can be a piece that is added to the distal hypotube 610, in which case the stinger 611 can be attached to the distal hypotube 610 in any suitable manner, for example by welding, soldering, by using adhesive, by mechanical engagement or by any combination of these methods.

The stinger 611 can extend proximally to come into contact with a distal portion of the proximal hypotube 601. In FIG. 6, the proximal hypotube has a cut-out or notch 603 formed in it, for example in one or both sides of the hypotube. This cut-out or notch 603 can be sized and configured to receive the stinger 611. In addition, the stinger 611 can be attached in the cut-out or notch 603, for example by welding, soldering, the use of adhesive, by mechanical interlock, or by any combination of these methods. In other embodiments, the stinger 611 could have cut-outs or grooves formed in it that are shaped and configured to accommodate the proximal hypotube distal end 602. The stinger 611 can allow for the elongate support member to transmit axial force down the shaft of the catheter. For example, axial force placed on the proximal hypotube in the distal direction can be transmitted through the stinger 611 and on to the tubular portion of the distal hypotube 610, and further on to the distal portion and distal tip of the device.

Turning to FIG. 6A, a cross-sectional view of the device of FIG. 6 is shown. The stinger 611 is shown extending back to the proximal hypotube 601, and the inflation tube 210 is shown surrounding the stinger 611 and the distal end 602 of the proximal hypotube 601. As seen in FIG. 6A, a portion of the stinger 611 can assume a slightly flattened profile, for example in order to engage the cut-out or notch 603.

In FIG. 7, a device that is similar in most respects to that shown in FIG. 6 is shown with an alternate method of connecting of a stinger 611 to a proximal hypotube 601. In this example, a distal portion of the stinger 611 is in contact with, and in some cases, attached to, the outer surface the proximal hypotube distal end 602 at an attachment point 703. The stinger 611 and the proximal hypotube 601 can be attached using, for example, welding, soldering, adhesive or mechanical engagement or interlock. FIG. 7A shows a cross-sectional view of a portion of the embodiment of FIG. 7. As shown in this figure, the inner surface of the stinger 611 and the outer surface of the proximal hypotube 601 can be in contact around at least a portion of the circumference of the proximal hypotube 601. It is also contemplated that the stinger 611 can be similarly attached to the inside of the proximal hypotube 601, in which case the inner surface of the distal end 602 of the proximal hypotube 601 can be in contact with and/or attached to the outer surface of the stinger 611 in a similar manner as described above.

In similar fashion, the proximal hypotube 601 can have a stinger that extends distally to come into contact with, and can be attached to the distal hypotube 610. The stinger can be similar to any of the stingers described above, and can be attached to the distal hypotube 610 in a fashion similar to that described above. In addition, both the proximal and distal hypotubes (601, 610) can have stingers (for example, any of the stingers described herein), and the stingers can be attached to one another (for example, using any of the methods of attachment described herein). In one example, the stingers can extend toward one another and form a lap joint between one another. In another example, the stingers can extend toward one another and be joined to one another in a crossed pattern. In such a case, one or both of the stingers could be twisted and/or bent so that the ends of the stingers are brought into contact with one another. In some cases, the stingers can be perpendicular to one another where they are joined to one another, and a cross section of the joint can take the form of an "X" shape.

Turning to FIG. 8, a device that is similar in many respects to that of FIGS. 6 and 7 is shown with an alternate connecting structure 880 between the proximal and distal hypotubes (601, 610). In this case, the elongate support member can have a plug 880 of material between the proximal hypotube distal end 602 and the distal hypotube proximal end 612. This plug 880 of material can be, for example, a plug or web of polymer that can be disposed between the two hypotubes so that the hypotubes can effectively transmit longitudinal force down the catheter shaft. The plug 880 of material can be formed by placing an insert of material (e.g., a polymer) between the members, softening or partially melting the material, and forcing the respective ends of the hypotubes (601, 610) into engagement with the plug 880. Further, the insert can be a portion of other members of the device, for example a portion of the guidewire tube 220 that has been folded back into a position in which it can form the plug 880. When the plug 880 hardens, it can form a connecting member between the proximal and distal hypotubes (601, 610).

Further, FIG. 8A shows a cross-sectional view of a portion of the device of FIG. 8. As shown in this figure, the plug 880 can be disposed within just a portion of the inflation lumen 211 so that fluids can still flow around the plug 880.

Turning to FIGS. 9 and 9A, an alternate embodiment of a catheter is shown. The distal hypotube 610 can extend proximally to attach to the proximal hypotube 601. The distal hypotube can be attached directly to the surface of the proximal hypotube 601, or it can be attached to the additional tubular member and/or coating 203. The proximal hypotube 601 can also have a spacer or other member attached at a point or around the circumference of the proximal hypotube 601 near the proximal hypotube distal end 602. The distal hypotube 610 can then be attached to this spacer or other member. Different spacers or other members can accommodate distal hypotubes of different inner diameters. The attachment of the distal and proximal hypotubes (601, 610) can be facilitated by, for example, welding, soldering, by using adhesive, by mechanical engagement or by any combination of these methods.

In the embodiments shown in FIGS. 9 and 9A, the inflation tube 210 can be a tubular member and/or coating that is disposed over all or a portion of the distal hypotube 610. The inflation tube can be disposed directly on the surface of the distal hypotube is 610. Further, the guidewire tube 220 proximal end can form a port 224 in the side of the inflation tube 210 and the distal hypotube 610. This port can be similar to any of the ports described herein. The guidewire tube 220 can extend distally within the lumen of the distal hypotube 610. For example, the guidewire tube 220 can extend distally in a coaxial fashion with respect to the distal hypotube 610 and/or the inflation tube 210. In some cases, the guidewire tube 220 can extend from the side port 224 to the distal end of the catheter, providing a guidewire passageway. In some cases, a lumen can be defined by the inside surface of the distal hypotube 610 and the outside surface of the guidewire tube 220. This lumen can be annular in shape, and can be an inflation lumen 211 that can allow for fluid communication between a proximal portion of the catheter and a distal portion of the catheter, for example a balloon or other device on a distal portion of the catheter.

It is noted that the proximal and distal hypotubes (601, 610) can be similar to any of the proximal and distal hypotubes described herein. In addition, the structures of FIGS. 9 and 9A can be similar in other respects to any of the embodiments that are described herein.

In FIGS. 6-9A, the elongate support member can be similar in many respects to the elongate support members discussed throughout this application. For example, the apertures 240 shown in FIGS. 6, 7, and 8 can be similar in size, shape, or distribution, or other attributes, to any of the apertures discussed herein. In some cases, apertures can be formed in the elongate support member such that fluid communication is allowed between a lumen in the proximal hypotube, the inflation lumen 211 and a balloon. In some examples, the distal hypotube can have a larger diameter, for example a larger inner diameter, than the proximal hypotube. Further, some embodiments can have a cuts or apertures formed in a stinger in order to provide a desired level of flexibility.

In at least some embodiments, portions of the length of, or the entire length of, the catheter 20 may be doped with, made of, or otherwise include a radiopaque material. Radiopaque materials are understood to be materials capable of producing a relatively bright image on a fluoroscopy screen or another imaging technique during a medical procedure. This relatively bright image aids the user of the device in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of catheter 20, for example the bands 230 shown in FIGS. 2 and 3.

In some embodiments, a degree of MRI compatibility is imparted into catheter 20. For example, to enhance compatibility with Magnetic Resonance Imaging (MRI) machines, it may be desirable to make hypotube 201, the inflation tube 210, the guidewire tube 220, or any combination thereof, in a manner that would impart a degree of MRI compatibility. For example, hypotube 201, the inflation tube 210, the guidewire tube 220, or portions thereof, may be made of a material that does not substantially distort the image and create substantial artifacts (artifacts are gaps in the image). Certain ferromagnetic materials, for example, may not be suitable because they may create artifacts in an MRI image. Hypotube 201, the inflation tube 210, the guidewire tube 220, or portions thereof, may also be made from a material that the MRI machine can image. Some materials that exhibit these characteristics include, for example, tungsten, Elgiloy, MP35N, Nitinol, and the like, and others.

It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

What is claimed is:

1. A balloon catheter comprising:
a hypotube defining a first lumen and having a proximal end and a distal end and a proximal portion and a distal portion adjacent the proximal and distal ends respectively;
a balloon attached to the hypotube near the hypotube distal end;
a guidewire tube having a proximal end and a distal end, the proximal end of the guidewire tube forming a guidewire port with the hypotube, the guidewire tube extending through an opening in the hypotube and distally within the hypotube, defining a guidewire lumen; and
an annular inflation lumen defined within the distal portion of the hypotube and formed between the hypotube and the guidewire tube;
wherein the balloon is attached to the hypotube by an inflation tube;
wherein a portion of the hypotube extends within a lumen of the inflation tube;
wherein the guidewire tube extends through a side wall of the inflation tube.

2. The balloon catheter of claim 1, wherein the hypotube has one or more cuts formed in the proximal portion and one or more cuts formed in the distal portion, the one or more cuts of the proximal portion differing from the one or more cuts of the distal portion in at least one of the following characteristics: cut density, cut shape, cut angle, placement of the one or more cuts relative to one another, and a type of cut.

3. The balloon catheter of claim 2, wherein the one or more cuts in the proximal portion comprise a plurality of apertures of a first density and the one or more cuts in the distal portion comprise a plurality of apertures of a second density, the first density and the second density being different.

4. The balloon catheter of claim 3, wherein the second density is greater than the first density.

5. The balloon catheter of claim 2, wherein the one or more cuts in the proximal portion comprise a plurality of apertures and the one or more cuts in the distal portion comprises one or more spiral cuts.

6. The balloon catheter of claim 2, wherein a portion of the one or more cuts is covered with a tubular member.

7. The balloon catheter of claim 2, wherein a portion of the one or more cuts is covered with a coating material.

8. The balloon catheter of claim 1, wherein the opening comprises a cut out portion of the hypotube.

9. The balloon catheter of claim 1, wherein the distal end of the balloon is fixed to a distal portion of the guidewire tube.

10. The balloon catheter of claim 9, wherein the guidewire tube further comprises one or more radiopaque markers.

11. The balloon catheter of claim 10, wherein the one or more radiopaque markers are located within the balloon.

12. The balloon catheter of claim 1, wherein the hypotube further comprises a stinger joining the proximal portion and the distal portion.

13. The balloon catheter of claim 12, wherein the guidewire tube enters the lumen of the hypotube in the vicinity of the stinger.

14. A balloon catheter comprising:
a hypotube defining a first lumen and having a proximal end and a distal end and a proximal portion and a distal portion adjacent the proximal and distal ends respectively;

a balloon attached to the hypotube near the hypotube distal end;

a guidewire tube having a proximal end and a distal end, the proximal end of the guidewire tube forming a guidewire port with the hypotube, the guidewire tube extending through an opening in the hypotube and distally within the hypotube, defining a guidewire lumen; and an annular inflation lumen defined within the distal portion of the hypotube and formed between the hypotube and the guidewire tube;

wherein the opening comprises a space between two adjacent windings of a spiral cut portion of the hypotube.

15. The balloon catheter of claim 14, wherein the hypotube has one or more cuts formed in the proximal portion and one or more cuts formed in the distal portion, the one or more cuts of the proximal portion differing from the one or more cuts of the distal portion in at least one of the following characteristics: cut density, cut shape, cut angle, placement of the one or more cuts relative to one another, and a type of cut.

16. The balloon catheter of claim 15, wherein the one or more cuts in the proximal portion comprise a plurality of apertures of a first density and the one or more cuts in the distal portion comprise a plurality of apertures of a second density, the first density and the second density being different.

17. The balloon catheter of claim 16, wherein the second density is greater than the first density.

18. The balloon catheter of claim 15, wherein the one or more cuts in the proximal portion comprise a plurality of apertures and the one or more cuts in the distal portion comprises one or more spiral cuts.

19. The balloon catheter of claim 15, wherein a portion of the one or more cuts is covered with a tubular member.

20. The balloon catheter of claim 15, wherein a portion of the one or more cuts is covered with a coating material.

* * * * *